(12) United States Patent
Christman et al.

(10) Patent No.: US 9,665,213 B2
(45) Date of Patent: May 30, 2017

(54) DETECTING PRESSURE EXERTED ON A TOUCH SURFACE AND PROVIDING FEEDBACK

(71) Applicant: Maxim Integrated Products, Inc., San Jose, CA (US)

(72) Inventors: Daniel S. Christman, Campbell, CA (US); Arpit Mehta, Fremont, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 100 days.

(21) Appl. No.: 14/463,699

(22) Filed: Aug. 20, 2014

(65) Prior Publication Data
US 2015/0062078 A1    Mar. 5, 2015

Related U.S. Application Data

(60) Provisional application No. 61/871,934, filed on Aug. 30, 2013.

(51) Int. Cl.
| | | |
|---|---|---|
| *A61B 5/00* | (2006.01) | |
| *A61B 5/024* | (2006.01) | |
| *A61B 5/1455* | (2006.01) | |
| *G06F 3/042* | (2006.01) | |
| *G06F 3/044* | (2006.01) | |

(52) U.S. Cl.
CPC ........ *G06F 3/0425* (2013.01); *A61B 5/14551* (2013.01); *A61B 5/6826* (2013.01); *A61B 5/6897* (2013.01); *G06F 3/044* (2013.01); *A61B 2562/0247* (2013.01); *G06F 2203/04105* (2013.01)

(58) Field of Classification Search
CPC ........ A61B 2562/0247; A61B 5/14551; A61B 5/6826; A61B 5/6897; A61B 5/02416; A61B 5/6843; A61B 5/7203; A61B 5/7275; A61B 5/0002; A61B 5/14532; A61B 5/0022; A61B 5/486; A61B 5/021; G06F 2203/04105; G06F 3/0425; G06F 3/044
See application file for complete search history.

(56) References Cited

U.S. PATENT DOCUMENTS

| | | | | |
|---|---|---|---|---|
| 6,327,376 B1 * | 12/2001 | Harkin | ................... | G01B 7/004 356/71 |
| 2003/0044051 A1 * | 3/2003 | Fujieda | ............. | G06K 9/00899 382/124 |
| 2007/0078316 A1 * | 4/2007 | Hoarau | ............. | A61B 5/14552 600/323 |

(Continued)

*Primary Examiner* — Hong Zhou
(74) *Attorney, Agent, or Firm* — Advent, LLP

(57) ABSTRACT

A system includes a sensor device configured to detect a touch pressure dependent characteristic of a body part of a user while the user touches a touch surface with the body part. The system also includes an image capture device configured to capture an image of the body part of the user while the user touches the touch surface. The system further includes a processor configured to associate the image with an amount of pressure exerted on the touch surface by the user. The processor is also configured to compare the amount of pressure exerted on the touch surface to a desired amount of pressure associated with the user for the sensor device, and initiate compensation for the touch pressure dependent characteristic based upon the comparison.

18 Claims, 5 Drawing Sheets

(56) References Cited

U.S. PATENT DOCUMENTS

| | | | |
|---|---|---|---|
| 2008/0166028 A1* | 7/2008 | Turek | G06K 9/0002 |
| | | | 382/124 |
| 2008/0262327 A1 | 10/2008 | Kato | |
| 2008/0306363 A1 | 12/2008 | Chaiken et al. | |
| 2009/0115727 A1* | 5/2009 | Wu | A61B 5/024 |
| | | | 345/163 |
| 2009/0203998 A1* | 8/2009 | Klinghult | A61B 5/02416 |
| | | | 600/443 |
| 2009/0232367 A1* | 9/2009 | Shinzaki | G06K 9/0012 |
| | | | 382/124 |
| 2009/0312654 A1* | 12/2009 | Kasama | G06F 3/042 |
| | | | 600/500 |
| 2011/0090047 A1* | 4/2011 | Patel | G07C 9/00158 |
| | | | 340/5.82 |
| 2011/0129128 A1* | 6/2011 | Makimoto | G06K 9/00013 |
| | | | 382/124 |
| 2013/0194236 A1* | 8/2013 | Gu | A61B 1/00172 |
| | | | 345/175 |
| 2013/0215042 A1* | 8/2013 | Messerschmidt | G06F 3/041 |
| | | | 345/173 |
| 2013/0296665 A1 | 11/2013 | Kassim et al. | |

* cited by examiner

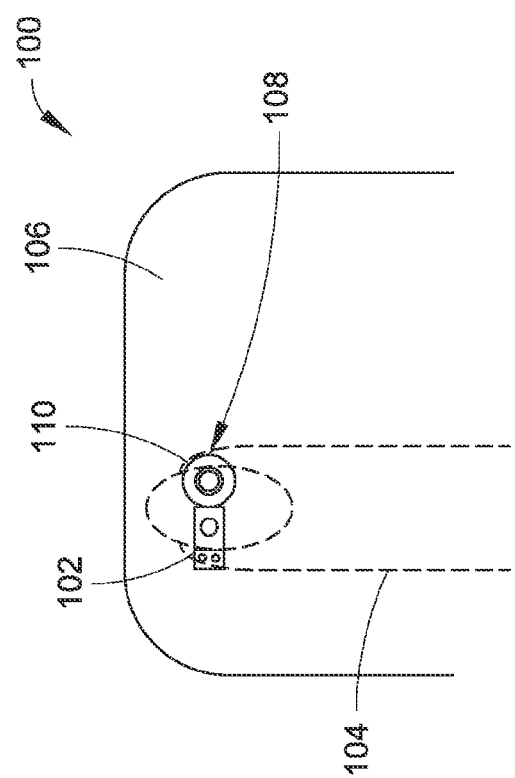
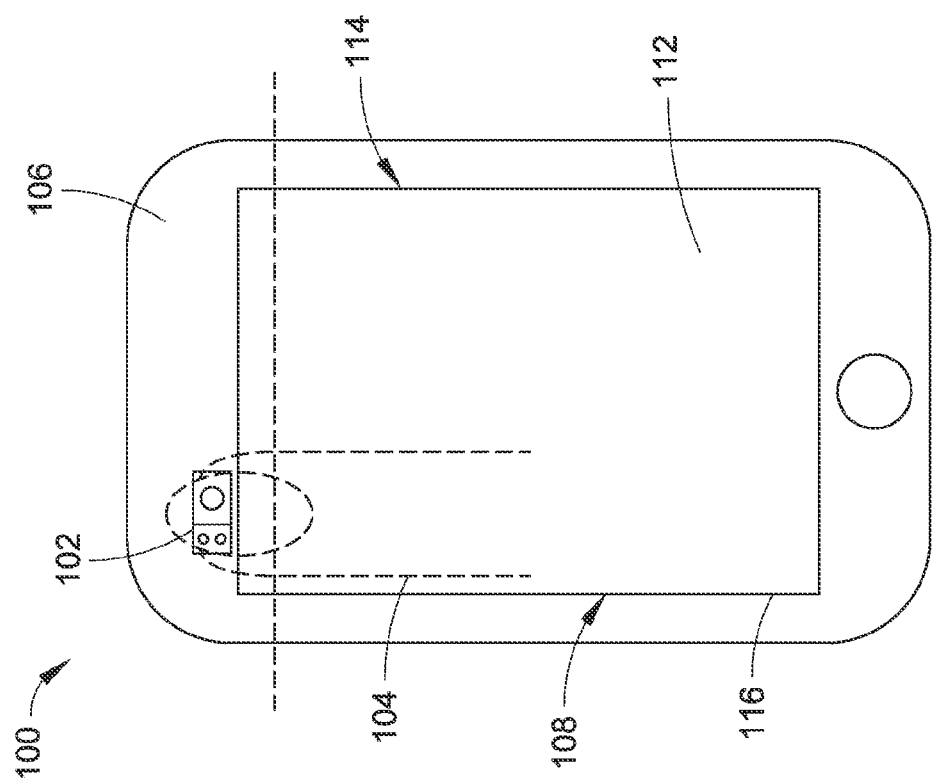
FIG. 3
FIG. 2

DETECTING PRESSURE EXERTED ON A TOUCH SURFACE AND PROVIDING FEEDBACK

CROSS-REFERENCE TO RELATED APPLICATIONS

The present application claims the benefit under 35 U.S.C. §119(e) of U.S. Provisional Application Ser. No. 61/871,934, filed Aug. 30, 2013, and titled "DETECTING PRESSURE EXERTED ON A TOUCH SURFACE AND PROVIDING FEEDBACK," which is herein incorporated by reference in its entirety.

BACKGROUND

A touch panel is a human machine interface (HMI) that allows an operator of an electronic device to provide input to the device using an instrument such as a finger, a stylus, and so forth. For example, the operator may use his or her fingers to manipulate images on an electronic display, such as a display attached to a mobile computing device, a personal computer (PC), or a terminal connected to a network. In some cases, the operator may use two or more fingers simultaneously to provide unique commands, such as a zoom command, executed by moving two fingers away from one another; a shrink command, executed by moving two fingers toward one another; and so forth. In other cases, the operator may use a stylus to provide commands via a touch panel.

A touch screen is an electronic visual display that incorporates a touch panel overlying a display to detect the presence and/or location of a touch within the display area of the screen. Touch screens are common in devices such as all-in-one computers, tablet computers, satellite navigation devices, gaming devices, and smartphones. A touch screen enables an operator to interact directly with information that is displayed by the display underlying the touch panel, rather than indirectly with a pointer controlled by a mouse or touchpad. Capacitive touch panels are often used with touch screen devices. A capacitive touch panel generally includes an insulator, such as glass, coated with a transparent conductor, such as indium tin oxide (ITO). As the human body is also an electrical conductor, touching the surface of the panel results in a distortion of the panel's electric field, measurable as a change in capacitance.

SUMMARY

A system includes a sensor device configured to detect a touch pressure dependent characteristic of a body part of a user while the user touches a touch surface with the body part. The system also includes an image capture device configured to capture an image of the body part of the user while the user touches the touch surface. The system further includes a processor configured to associate the image with an amount of pressure exerted on the touch surface by the user. The processor is also configured to compare the amount of pressure exerted on the touch surface to a desired amount of pressure associated with the user for the sensor device, and initiate compensation for the touch pressure dependent characteristic based upon the comparison. For example, one or more instructions can be initiated that instruct the user to move the body part to adjust the amount of pressure exerted on the touch surface toward the desired amount of pressure associated with the user. Further, a signal that measures the touch pressure dependent characteristic can also be modified based upon the comparison.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 1 is a partial diagrammatic illustration of a system configured to initiate compensation for a touch pressure dependent characteristic detectable by the system, where the system can be configured to instruct a user to move a body part, such as a fingertip, to adjust the amount of pressure the user exerts on a touch surface and/or to modify a signal that measures the touch pressure dependent characteristic in accordance with an example embodiment of the present disclosure.

FIG. 2 is a diagrammatic illustration of the system illustrated in FIG. 1, where the system includes a touch screen in accordance with an example embodiment of the present disclosure.

FIG. 3 is a diagrammatic illustration of a system configured to initiate compensation for a touch pressure dependent characteristic detectable by the system, where the system can be configured to instruct a user to move a body part, such as a fingertip, to adjust the amount of pressure the user exerts on a touch surface and/or to modify a signal that measures the touch pressure dependent characteristic, and where the system includes a camera in accordance with an example embodiment of the present disclosure.

DETAILED DESCRIPTION

Figure 1:
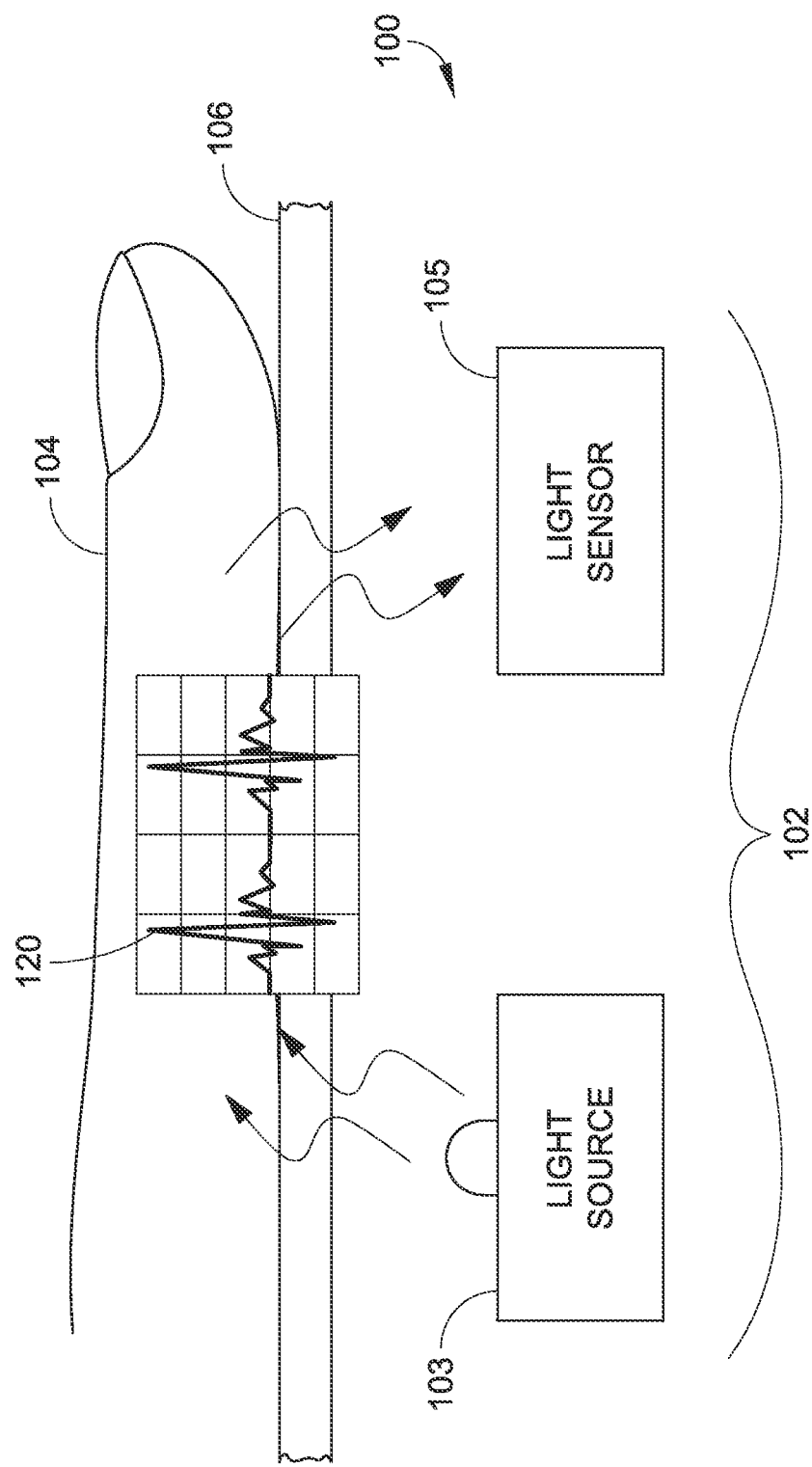

Sensor devices that provide user monitoring functionality can be included in portable electronic devices, such as smartphones, portable health monitors, and so forth. These portable devices can be used to detect (e.g., measure) health and/or biological characteristics of a user, such as blood oxygen saturation, blood glucose concentration, and so on. Some sensor devices require a user to touch a substrate supporting a sensor in order to perform a detection operation. However, such sensor devices can be sensitive to pressure variations when the user touches the substrate. For example, a fingertip sensor device is calibrated to perform detection operations at a particular pressure exerted by the touch of the user's fingertip. When the user touches the substrate and exerts a different pressure, the results of the detection operation can be affected. For example, the results can be less accurate than when a desired level of pressure is exerted. Further, finger pressure can vary from person to person, and the signal strength received by a sensor can vary accordingly.

Systems and techniques are described that initiate compensation for a touch pressure dependent characteristic detectable by a system. In some embodiments, instructions are provided to a user when the user exerts pressure on a touch surface with a body part. For example, the systems determine finger pressure by determining an area pressed by a finger and instruct the user to move the finger to adjust the amount of pressure the user exerts on the touch surface. The instructions are configured to instruct the user to adjust the amount of pressure the user exerts on a bio-signal sensor, and can reduce pressure artifacts, increase the signal-to-noise (SNR) ratio of bio-signal sensor output, and so forth. The systems can also modify a signal that measures the touch pressure dependent characteristic. In some embodiments, the systems comprise touch sensing systems, such as capacitive touch panels, touch screens, and so forth. In some embodiments, the systems comprise one or more cameras. As described herein, a system can be configured as a smart phone, a tablet computing device, a health monitor (e.g., a health monitor band), a fitness monitor (e.g., a fitness monitor band), and so forth. In example embodiments, the systems described herein can be used with smart phone camera and/or touch screen devices.

FIGS. 1 through 4 illustrate example systems 100 in accordance with example implementations of the present disclosure. The systems 100 include a bio-signal sensor device (e.g., a pulse oximeter sensor device 102, a heart rate monitor device, and so forth) configured to detect a touch pressure dependent characteristic of a body part (e.g., a finger 104) of a user while the user touches a touch surface 106 with the body part. For example, the touch surface 106 comprises the housing of a smart phone, and the pulse oximeter sensor device 102 is configured as an integrated circuit (IC) chip comprising a light source 103 (e.g., a red wavelength light emitting diode (LED), an infrared (IR) LED, and so forth) and a light sensor 105 (e.g., a photodiode sensor) positioned under a glass touch surface 106. However, a smart phone is provided by way of example only and is not meant to limit the present disclosure. In other embodiments, the touch surface 106 is comprised of a tablet computing device, a health monitor (e.g., a health monitor band), a fitness monitor (e.g., a fitness monitor band), and so forth.

In some embodiments, the pulse oximeter sensor device 102 comprises a transmission pulse oximeter that transmits light through the finger 104. In other embodiments, the pulse oximeter sensor device 102 comprises a reflection pulse oximeter that reflects light from the finger 104. However, the pulse oximeter sensor device 102, the light source 103, and the light sensor 105 are provided by way of example only and are not meant to be restrictive of the present disclosure. In other embodiments, a bio-signal sensor can be configured to detect one or more of oxygen ($O_2$) saturation, a glucose concentration, a carbon monoxide (CO) concentration, a carbon dioxide ($CO_2$) concentration associated with blood in the body part of the user, and so forth. In some embodiments the bio-signal sensor can implement one or more sensor functionalities, including, but not necessarily limited to, a glucose sensor, a heart rate sensor (e.g., a heart rate monitor that uses a red LED, a green wavelength LED, an IR LED, another color wavelength emitting LED, a multi-color wavelength emitting LED, and so on, with one or more associated light sensors, and so forth).

The system 100 includes an image capture device 108 configured to capture at least a partial image (e.g., a partial image, a full image, etc.) of the finger 104 of the user while the user touches the touch surface 106 with the finger 104. In some embodiments, the image capture device 108 comprises a camera 110 configured to detect light in the visible spectrum. In other embodiments, the camera 110 is configured to detect light in the IR spectrum (e.g., as reflected from the pulse oximeter sensor device 102). In still further embodiments, the camera 110 detects light in both the visible spectrum and the IR spectrum. In some embodiments, images captured by the camera are grayscale (e.g., shades of gray, black and white, etc.). In other embodiments, images captured by the camera are in color.

In other embodiments, the image capture device 108 comprises a touch panel 112. For example, the systems 100 include one or more touch panels 112, such as mutual capacitance Projected Capacitive Touch (PCT) panels. The capacitive touch panels 112 are configured to sense multiple inputs simultaneously, or at least substantially simultaneously. The capacitive touch panels 112 can be included with electronic devices, including, but not necessarily limited to: large touch panel products, touchpad products, all-in-one computers, mobile computing devices (e.g., hand-held portable computers, Personal Digital Assistants (PDAs), laptop computers, netbook computers, tablet computers, and so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, as well as with other devices that employ touch-based human interfaces.

The capacitive touch panels 112 can comprise ITO touch panels 112 that include drive electrodes, such as X-axis and/or Y-axis cross-bar ITO drive traces/tracks, arranged next to one another (e.g., along parallel tracks, generally parallel tracks, and so forth). The drive electrodes are elongated (e.g., extending along a longitudinal axis). For example, each drive electrode extends along an axis on a supporting surface, such as a substrate of a capacitive touch panel 112. The capacitive touch panels 112 also include sense electrodes, such as cross-bar X-axis and/or Y-axis ITO sensor traces/tracks, arranged next to one another across the drive electrodes (e.g., along parallel tracks, generally parallel tracks, and so forth). The sense electrodes are elongated (e.g., extending along a longitudinal axis). For instance, each sense electrode extends along an axis on a supporting surface, such as a substrate of a capacitive touch panel 112. It should be noted that an ITO touch panel 112 is provided by way of example only and is not meant to limit the present disclosure. In other embodiments, one or more other transparent materials (e.g., Antimony Tin Oxide (ATO)), semi-transparent materials, and/or non-transparent materials (e.g., copper) is used for a drive electrode and/or a sense electrode of a capacitive touch panel.

The drive electrodes and the sense electrodes define a coordinate system where each coordinate location (pixel) comprises a capacitor formed at each junction between one of the drive electrodes and one of the sense electrodes. Thus, the drive electrodes are configured to connect to one or more electrical circuits and/or electronic components (e.g., one or more drivers) to generate a local electric field at each capacitor. A change in the local electric field generated by an instrument (e.g., input from a finger or a stylus) at each capacitor formed at a drive electrode and a sense electrode causes a change (e.g., a decrease) in capacitance associated with a touch at the corresponding coordinate location. Mutual capacitance is capacitance that occurs between two charge-holding objects (e.g., conductors). In this instance, mutual capacitance is the capacitance between the drive electrodes and the sense electrodes that comprise the capacitive touch panel sensor. As described above, the drive electrodes and the sense electrodes comprise traces that represent the driving lines and corresponding sensing lines to detect a change in mutual capacitance due to a touch event performed over the surface of the touch panel 112. It should be noted that for the purposes of the present disclosure, the drive electrodes comprise the driving lines and the sense electrodes comprise the sensing lines in some implementations, and the drive electrodes comprise the sensing lines and the sense electrodes comprise the driving lines in other implementations.

It should also be noted that capacitive touch panels 112 as described herein are not limited to mutual capacitance sensing. For example, input from a finger can also be sensed via self capacitance of one or more of the capacitive touch panel sensors. Self capacitance is the capacitance associated with the respective column and the respective row and represents the amount of electrical charge to be furnished to the respective column or row to raise its electrical potential by one unit (e.g., by one volt, and so on). In embodiments of the disclosure, more than one touch can be sensed at differing coordinate locations simultaneously (or at least substantially simultaneously). In some embodiments, the drive electrodes are driven by one or more of the drivers in parallel, e.g., where a set of different signals are provided to the drive electrodes. In other embodiments, the drive electrodes are driven by one or more of the drivers in series, e.g., where each drive electrode or subset of drive electrodes is driven one at a time.

The sense electrodes are electrically insulated from the drive electrodes (e.g., using a dielectric layer, and so forth). For example, the sense electrodes are provided on one substrate (e.g., comprising a sense layer disposed on a glass substrate), and the drive electrodes are provided on a separate substrate (e.g., comprising a drive layer disposed on another substrate). In this two-layer configuration, the sense layer can be disposed above the drive layer (e.g., with respect to a touch surface). For example, the sense layer is positioned closer to a touch surface than the drive layer. However, this configuration is provided by way of example only and is not meant to be restrictive of the present disclosure. Thus, other configurations can be provided where the drive layer is positioned closer to a touch surface than the sense layer, and/or where the sense layer and the drive layer comprise the same layer. For instance, in a 1.5-layer embodiment (e.g., where the drive layer and the sense layer are included on the same layer but physically separated from one another), one or more jumpers are used to connect portions of a drive electrode together. Similarly, jumpers can be used to connect portions of a sense electrode together. In other embodiments, the drive layer and the sense layer comprise the same layer (e.g., in a single-layer sensor configuration).

One or more capacitive touch panels 112 can be included with a touch screen assembly 114. The touch screen assembly 114 includes a display screen 116, such as a liquid crystal display (LCD) screen, where the sense layer and the drive layer are sandwiched between the LCD screen and a bonding layer, with a protective cover (e.g., cover glass) attached thereto. The cover glass can include a protective coating, an anti-reflective coating, and so forth. The cover glass comprises a touch surface, upon which an operator can use one or more fingers, a stylus, and so forth to input commands to the touch screen assembly 114. The commands can be used to manipulate graphics displayed by, for example, the LCD screen. Further, the commands can be used as input to an electronic device connected to a capacitive touch panel 112, such as a multimedia device or another electronic device (e.g., as previously described).

Figure 5:
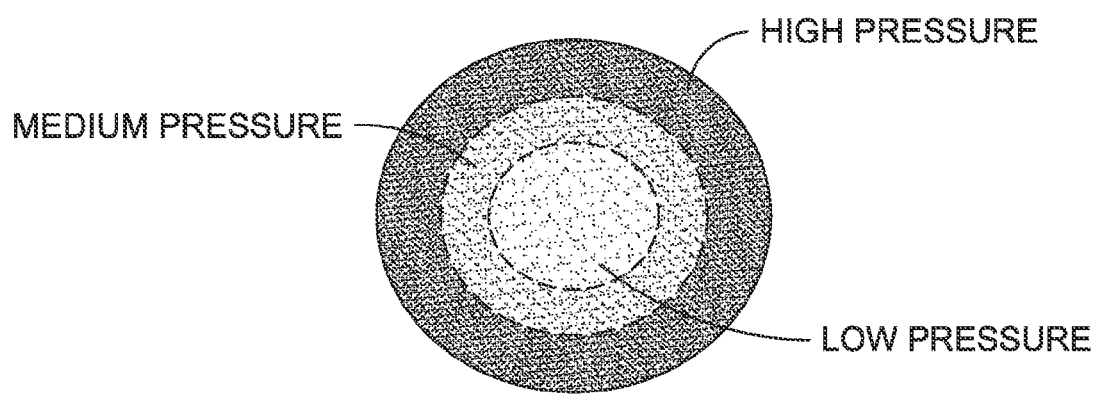
FIG. 5 is a diagrammatic illustration of finger pressure profiles in accordance with example embodiments of the present disclosure.
Figure 8:
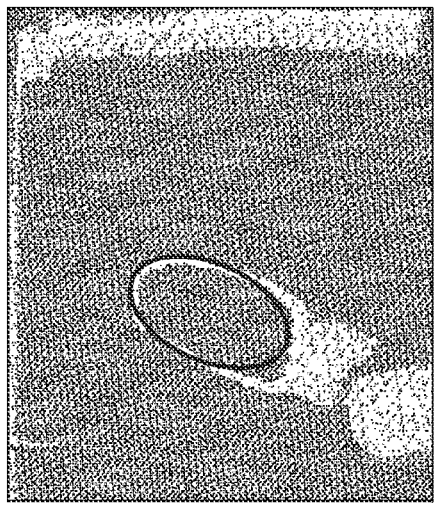
FIG. 8 is an image of a finger pressing on a transparent glass substrate with comparatively heavy pressure, where the heavy pressure exerted by the finger on the glass is determined by identifying the area of the glass pressed by the finger in accordance with an example embodiment of the present disclosure.
Figure 7:
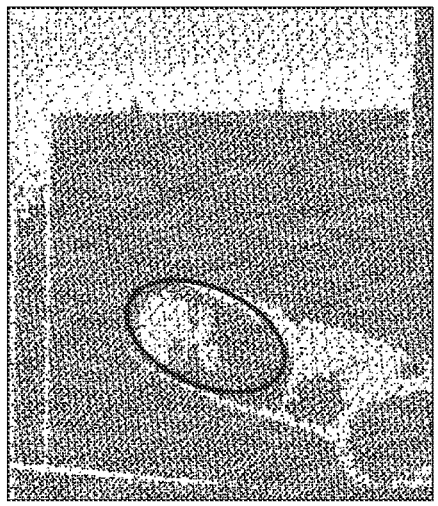
FIG. 7 is an image of a finger pressing on a transparent glass substrate with comparatively medium pressure, where the medium pressure exerted by the finger on the glass is determined by identifying the area of the glass pressed by the finger in accordance with an example embodiment of the present disclosure.
Figure 6:
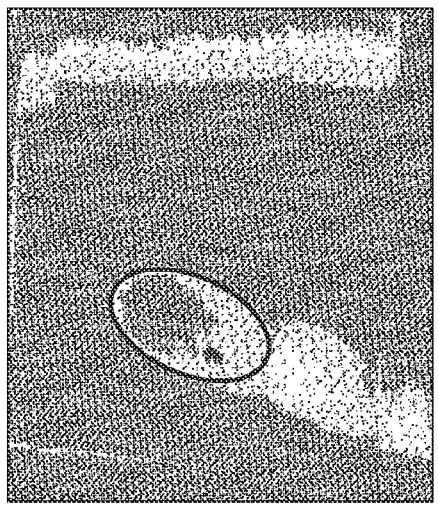
FIG. 6 is an image of a finger pressing on a transparent glass substrate with comparatively light pressure, where the light pressure exerted by the finger on the glass is determined by identifying the area of the glass pressed by the finger in accordance with an example embodiment of the present disclosure.

The system 100 includes a processor 150 configured to associate images from the image capture device 108 with an amount of pressure exerted on the touch surface 106 by the user. For example, an image is associated with an amount of pressure exerted on the touch surface 106 by determining an area of the touch surface 106 pressed by the finger 104, e.g., as described with reference to FIG. 5, where different pressure profiles captured by the image capture device 108 (e.g., a touch screen, a camera, etc.) are schematically illustrated. With reference to FIGS. 6 through 8, images of a finger pressing on a transparent glass substrate with different pressures are described. In these examples, an amount of pressure exerted by the finger on the glass can be determined by identifying an area of the glass pressed by the finger. For instance, in FIG. 6, comparatively light pressure is exerted, while in FIG. 7, comparatively medium pressure is exerted, and in FIG. 8, comparatively heavy pressure is exerted. In each case, the amount of pressure can be determined by identifying the area of the glass pressed by the finger. In further embodiments, the amount of pressure exerted on the touch surface 106 by the user can be determined by using a correlation between two or more programmable pattern generator (PPG) channels of the touch panel 112.

In some embodiments, pressure exerted on the touch surface 106 is proportional (e.g., directly proportional) to the surface area of the finger 104 in contact with the touch surface 106. Thus, images captured by the image capture device 108 (e.g., camera 110 and/or touch panel 112, and so forth) can be used to determine finger pressure. For instance, greater pressure exerted on the touch surface 106 corresponds to a larger area of finger contact with the touch panel 112, which produces electronic signals that can be used to determine the pressure exerted on the touch surface 106. Similarly, greater pressure exerted on the touch surface 106 can be detected by processing an image captured by the camera 110. In some embodiments, partial images of a body part captured by the camera 110 and/or the touch panel 112 can be used to determine finger pressure. For example, when the tip of a finger is placed on the pulse oximeter sensor device 102 as shown in FIG. 2, part of the fingertip also covers the touch screen assembly 114, and the area covering the touch screen assembly 114 is representative of the finger pressure applied.

The processor 150 of the system 100 is configured to compare the amount of pressure exerted on the touch surface 106 by the user to a desired amount of pressure associated with the user for the bio-signal sensor device. For example, a desired amount of pressure can be determined for a particular user or a group of users by calibrating the overall area of a user's finger detectable by one or more image capture devices 108. This calibration can be performed using an amount of pressure exerted on the touch surface 106 by a user when initial bio-signals are collected from the user (e.g., upon device startup, device initialization, and so forth). In some embodiments, these bio-signals are compared with bio-signals measured with another bio-sensor simultaneously, or substantially simultaneously. In other embodiments, bio-signals collected using the pulse oximeter sensor device 102 are compared to known (e.g., baseline) bio-signal information for the user. These comparisons are then used to determine a desired amount of pressure to be exerted by the user (e.g., a pressure that generates bio-signals within a desired range, having a certain degree of accuracy, and so forth). Further, such calibration can be performed for a particular size and/or range of sizes for a body part (e.g., finger size), a particular biological characteristic (e.g., profusion rate), and so forth.

In some embodiments, the processor 150 of the system 100 is configured to initiate an instruction to the user to move the finger 104 to adjust the amount of pressure exerted on the touch surface 106 toward the desired amount of pressure. For example, the system 100 is configured to instruct the user to move the finger 104 toward the desired amount of pressure associated with the user for the pulse oximeter sensor device 102. Accordingly, the system 100 includes an indicator 118 configured to provide instructions to move the finger 104. In some embodiments, the indicator 118 comprises the touch screen assembly 114. For instance, graphical instructions (e.g., directional arrows) can be provided that instruct the user to move the finger 104. However, graphical instructions are provided by way of example only and are not meant to limit the present disclosure. In other embodiments, the indicator 118 can provide audio instructions, tactile instructions, haptic feedback, and so on to instruct the user. For the purposes of the present disclosure, adjusting pressure exerted on the touch surface 106 includes increasing or decreasing an amount of surface area of a body part in contact with the touch surface 106, making a positional adjustment (e.g., finger placement) of a body part with respect to the touch surface 106, and so forth. For example, the instructions can be used to achieve consistent placement of the finger 104.

In some embodiments, the system 100 also includes a gyroscope, an accelerometer, and so forth, which can be used to reduce motion artifacts when sensing bio-signals. Further, the system 100 can be configured to adjust the current through a bio-signal sensor, such as the pulse oximeter sensor device 102, based upon a detected amount of pressure exerted by a user. For example, more current can be supplied based upon a detected pressure level to increase the SNR of the system 100 when bio-signals are detected. In some embodiments, current through the pulse oximeter sensor device 102 is adjusted in discrete steps. In other embodiments, the current is adjusted continuously, based upon values in a lookup table, and so forth. Further, it will be appreciated that the touch surface 106 and the image capture device 108 are not necessarily disposed on the same side of the housing of an electronic device, such as a smart phone. For example, the image capture device 108 and the pulse oximeter sensor device 102 are disposed on opposite sides (e.g., front and back sides) of a smart phone. Further, in some embodiments, another sensor is used to augment the pressure detecting capability of the system 100. For example, the system 100 includes a pressure sensor comprising an aperture defined in the touch surface 106 for sensing barometric pressure, where blockage of the aperture is associated with pressure exerted on the touch surface 106.

In some embodiments, a signal 120 is modified that measures the touch pressure dependent characteristic of the body part (e.g., the finger 104) of the user. For example, touch and/or pressure information detected by the system 100 can be used with one or more motion compensation algorithms that compensate for a touch pressure dependent characteristic (e.g., in a case where the user is rolling finger 104 across the touch surface 106, which may be detectable by a change in the capacitive image). In some embodiments, modifying the signal 120 comprises discarding data comprising a portion of the signal 120. In other embodiments, modifying the signal 120 comprises removing one or more artifacts from the signal 120. For example, when the signal 120 is undetectable and strong finger pressure is detected, updates are not provided. In this example, instructions are provided to the user to apply less pressure. When the signal 120 is weak but still detectable, then an attempt to use the data can be made, along with feedback to the user that the signal could be improved by applying less pressure. In another example, when a sudden change in finger pressure is detected (e.g., resulting in large artifacts), the data can be discarded during the abrupt change, and updating can resume when the artifact subsides, and/or an attempt can be made to compensate for the change in pressure.

In a further example, when finger rolling is detected, the data can be discarded, and the output can cease, and/or an attempt can be made to remove the artifact (e.g., using a motion compensation algorithm). In this example, feedback can be provided to the user stating that the finger 104 should be kept still. In another example, when an incorrect finger position is detected (e.g., using the camera 110), feedback can be provided to the user. In this example, if a weak signal is still present, an attempt can be made to use the signal; otherwise, output is not necessarily provided. In a still further example, when removal of the finger 104 is detected (e.g., using the camera 110), the data can be temporarily discarded, and updating can resume when the finger 104 is replaced. However, if the finger 104 is not replaced quickly, a reset operation may be performed while waiting for the signal 120 to resume. In another example, when motion consistent with walking motion and/or running motion of the user is detected (e.g., a harmonic change in pressure), an attempt can be made to remove artifacts from the signal (e.g., using a motion compensation algorithm).

Figure 4:
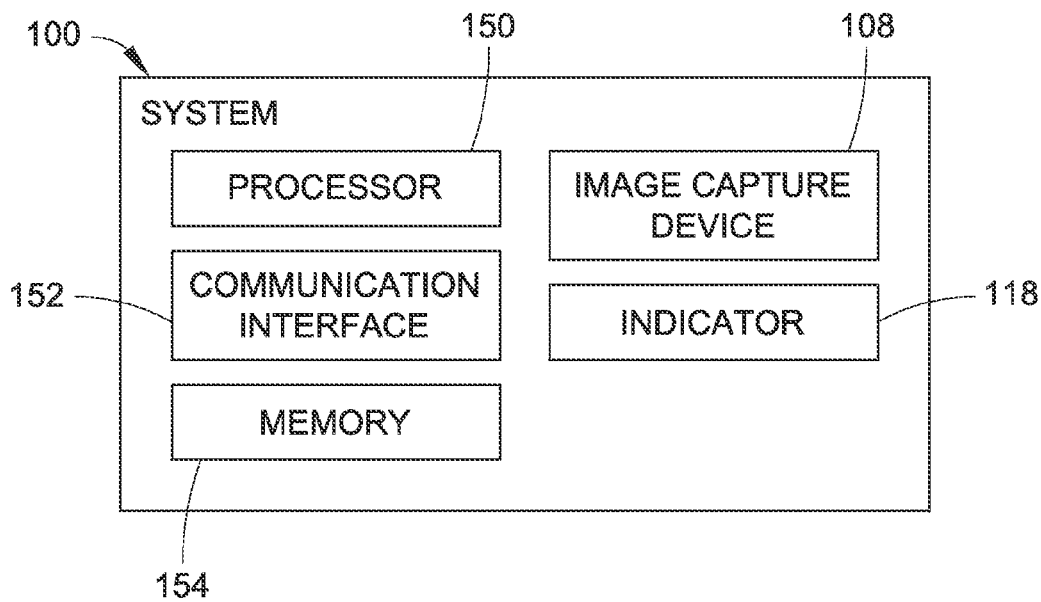
FIG. 4 is a block diagram illustrating a system configured to initiate compensation for a touch pressure dependent characteristic detectable by the system in accordance with an example embodiment of the present disclosure.

Referring now to FIG. 4, a system 100, including some or all of its components, can operate under computer control. For example, a processor 150 can be included with or in a system 100 to control the components and functions of systems 100 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 100. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

As described, the system 100 includes a processor 150, a communications interface 152, and a memory 154. The processor 150 provides processing functionality for the system 100 and can include any number of processors, micro-controllers, or other processing systems and resident or external memory for storing data and other information accessed or generated by the system 100. The processor 150 can execute one or more software programs, which implement techniques described herein. The processor 150 is not limited by the materials from which it is formed or the processing mechanisms employed therein, and as such, can be implemented via semiconductor(s) and/or transistors (e.g., using electronic Integrated Circuit (IC) components), and so forth. The communications interface 152 is operatively configured to communicate with components of the touch panel. For example, the communications interface 152 can be configured to control the drive electrodes and/or the sense electrodes of the touch panel, receive inputs from the sense electrodes and/or the drive electrodes of the touch panel, and so forth. The communications interface 152 is also communicatively coupled with the processor 150 (e.g., for communicating inputs from the sense electrodes of the capacitive touch panel to the processor 150).

The communications interface 152 and/or the processor 150 can be configured to communicate with a variety of different networks, including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, these networks are provided by way of example only and are not meant to limit the present disclosure. Further, the communications interface 152 can be configured to communicate with a single network or multiple networks across different access points.

The memory 154 is an example of tangible computer-readable media that provides storage functionality to store various data associated with operation of the system 100, such as software programs and/or code segments, or other data to instruct the processor 150 and possibly other components of the system 100 to perform the steps described herein. Thus, the memory 154 can store data, such as a program of instructions for operating the system 100 (including its components), and so forth. It should be noted that while a single memory 154 is shown, a wide variety of types and combinations of memory can be employed. The memory 154 can be integral with the processor 150, can comprise stand-alone memory, or can be a combination of both. The memory 154 can include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, and so forth. In embodiments, the system 100 and/or the memory 154 can include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

Figure 9:
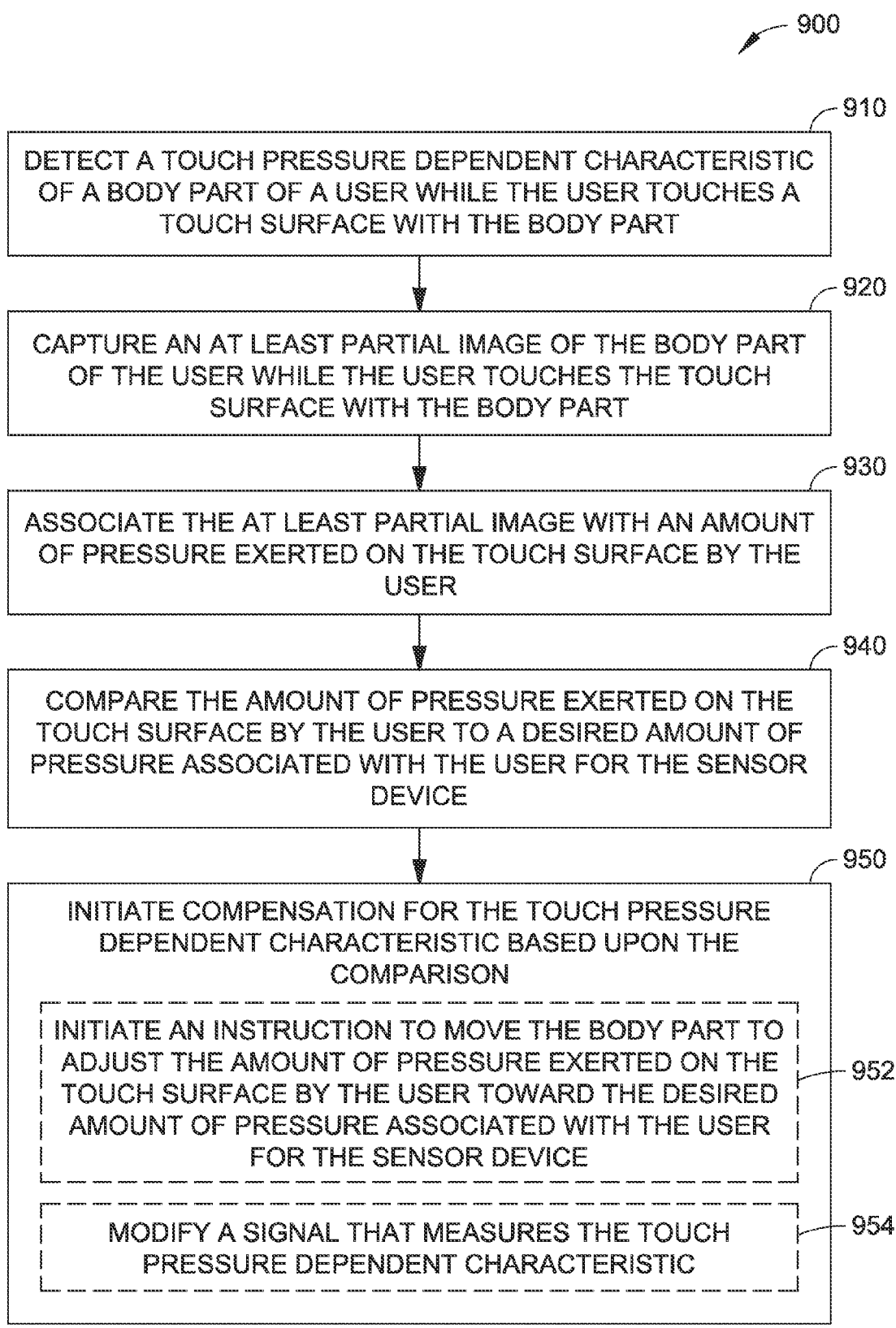
FIG. 9 is a flow diagram illustrating a method for initiating compensation for a touch pressure dependent characteristic in accordance with example embodiments of the present disclosure.

The following discussion describes example techniques for initiating compensation for a touch pressure dependent characteristic. FIG. 9 depicts a procedure 900, in example embodiments, in which instructions can be initiated to a user to instruct the user to move a body part, such as a fingertip, to adjust the amount of pressure the user exerts on a touch surface, and/or a signal that measures the touch pressure dependent characteristic can be modified. In the procedure 900 illustrated, a touch pressure dependent characteristic of a body part of a user is detected while the user touches a touch surface with the body part (Block 910). For example, with reference to FIGS. 1 through 4, pulse oximeter sensor device 102 positioned under touch surface 106 is used to measure oxygen saturation for a user when the user touches the touch surface 106 with finger 104. Then, at least a partial image of the body part of the user is captured while the user touches the touch surface with the body part (Block 920). For instance, with continuing reference to FIGS. 1 through 4, image capture device 108 captures an image (e.g., a partial image, a full image, etc.) of the finger 104 while the user touches the touch surface 106 with the finger 104.

Next, the at least partial image is associated with an amount of pressure exerted on the touch surface by the user (Block 930). For example, with continuing reference to FIGS. 1 through 4, processor 150 associates the image captured by the image capture device 108 with an amount of pressure exerted on the touch surface 106 by determining an area of the touch surface 106 pressed by the finger 104 (e.g., as described with reference to FIGS. 5 through 8). Then, the amount of pressure exerted on the touch surface by the user is compared to a desired amount of pressure associated with the user for the sensor device (Block 940). For instance, with continuing reference to FIGS. 1 through 4, the area of the touch surface 106 pressed by the finger 104 is compared to an overall area of the user's finger detectable by the image capture devices 108 (e.g., determined using a calibration operation).

Next, compensation is initiated for the touch pressure dependent characteristic based upon the comparison (Block 950). In some embodiments, an instruction is initiated to move the body part to adjust the amount of pressure exerted on the touch surface by the user toward the desired amount of pressure associated with the user for the sensor device (Block 952). For example, with continuing reference to FIGS. 1 through 4, indicator 118 (e.g., touch screen assembly 114) provides graphical instructions, such as directional arrows, that instruct the user to move the finger 104. In some embodiments, a signal is modified that measures the touch pressure dependent characteristic (Block 954). In some embodiments, modifying the signal that measures the touch pressure dependent characteristic comprises discarding data comprising a portion of the signal. In other embodiments, modifying the signal that measures the touch pressure dependent characteristic comprises removing an artifact from the signal (e.g., as previously described).

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A smart phone comprising:
a smart phone camera for capturing images of a surrounding environment;
a sensor device including a light source and a light sensor, the sensor device disposed under a touch surface adjacent to the smart phone camera, the sensor device configured to detect a touch pressure dependent characteristic of a body part of a user while the user touches the touch surface with the body part, the smart phone camera configured to capture a partial image of the body part of the user while the user touches the touch surface with the body part and the touch pressure dependent characteristic is detected; and
a processor configured to associate the partial image with an amount of pressure exerted on the touch surface by the user, compare the amount of pressure exerted on the touch surface by the user to a desired amount of pressure associated with the user for the sensor device, and initiate an instruction to move the body part to adjust the amount of pressure exerted on the touch surface by the user toward the desired amount of pressure associated with the user for the sensor device.

2. The smart phone as recited in claim 1, wherein the partial image is associated with the amount of pressure exerted on the touch surface by determining an area of the touch surface pressed by the body part.

3. The smart phone as recited in claim 1, wherein the sensor device comprises at least one of a pulse oximeter sensor device or a heart rate sensor device.

4. The smart phone as recited in claim 1, further comprising an indicator configured to provide the instruction to move the body part to the user.

5. The smart phone as recited in claim 1, wherein the touch pressure dependent characteristic of the user comprises at least one of an oxygen saturation, a glucose concentration, a carbon monoxide (CO) concentration, or a carbon dioxide ($CO_2$) concentration associated with blood in the body part of the user.

6. A smart phone comprising:
a smart phone camera for capturing images of a surrounding environment;
a sensor device including a light source and a light sensor, the sensor device disposed under a touch surface adjacent to the smart phone camera, the sensor device configured to detect a touch pressure dependent characteristic of a body part of a user while the user touches the touch surface with the body part, the smart phone camera configured to capture a partial image of the body part of the user while the user touches the touch surface with the body part and the touch pressure dependent characteristic is detected;
and
a processor configured to associate the partial image with an amount of pressure exerted on the touch surface by the user, compare the amount of pressure exerted on the touch surface by the user to a desired amount of pressure associated with the user for the sensor device, and initiate compensation for the touch pressure dependent characteristic based upon the comparison.

7. The smart phone as recited in claim 6, wherein initiating compensation for the touch pressure dependent characteristic comprises initiating an instruction to move the body part to adjust the amount of pressure exerted on the touch surface by the user toward the desired amount of pressure associated with the user for the sensor device.

8. The smart phone as recited in claim 6, wherein initiating compensation for the touch pressure dependent characteristic comprises modifying a signal that measures the touch pressure dependent characteristic.

9. The smart phone as recited in claim 8, wherein modifying the signal that measures the touch pressure dependent characteristic comprises discarding data comprising at least a portion of the signal.

10. The smart phone as recited in claim 8, wherein modifying the signal that measures the touch pressure dependent characteristic comprises removing an artifact from the signal.

11. The smart phone as recited in claim 6, wherein the partial image is associated with the amount of pressure exerted on the touch surface by determining an area of the touch surface pressed by the body part.

12. The smart phone as recited in claim 6, further comprising an indicator configured to provide the instruction to move the body part to the user.

13. A method comprising:
capturing, by a smart phone camera for capturing images of a surrounding environment, a partial image of a user;
detecting, by a sensor device including a light source and a light sensor, the sensor device disposed under a touch surface adjacent to the smart phone camera, a touch pressure dependent characteristic of a body part of a user while the user touches the touch surface with the body part, the partial image of the user including a partial image of the body part of the user captured while the user touches the touch surface with the body part and the touch pressure dependent characteristic is detected;
associating the partial image with an amount of pressure exerted on the touch surface by the user;
comparing the amount of pressure exerted on the touch surface by the user to a desired amount of pressure associated with the user; and initiating compensation for the touch pressure dependent characteristic based upon the comparison.

14. The method as recited in claim 13, wherein initiating compensation for the touch pressure dependent characteristic comprises initiating an instruction to move the body part to adjust the amount of pressure exerted on the touch surface by the user toward the desired amount of pressure associated with the user.

15. The method as recited in claim 13, wherein initiating compensation for the touch pressure dependent characteristic comprises modifying a signal that measures the touch pressure dependent characteristic.

16. The method as recited in claim 15, wherein modifying the signal that measures the touch pressure dependent characteristic comprises discarding data comprising at least a portion of the signal.

17. The method as recited in claim 15, wherein modifying the signal that measures the touch pressure dependent characteristic comprises removing an artifact from the signal.

18. The method as recited in claim 13, wherein the partial image is associated with the amount of pressure exerted on the touch surface by determining an area of the touch surface pressed by the body part.

* * * * *